(12) United States Patent
Schlueter et al.

(10) Patent No.: US 9,829,431 B2
(45) Date of Patent: Nov. 28, 2017

(54) FLOW REDUCTION SYSTEM FOR ISOTOPE RATIO MEASUREMENTS

(71) Applicant: Thermo Fisher Scientific (Bremen) GmbH, Bremen (DE)

(72) Inventors: Hans-Juergen Schlueter, Bremen (DE); Eric Wapelhorst, Bremen (DE); Nils Stoebener, Bremen (DE); Hans-Juerg Jost, Hilterfingen (CH); Tim Stoltmann, Grenoble (FR)

(73) Assignee: Thermo Fisher Scientific (Bremen) GmbH, Bremen (DE)

( * ) Notice: Subject to any disclaimer, the term of this patent is extended or adjusted under 35 U.S.C. 154(b) by 29 days.

(21) Appl. No.: 15/142,329

(22) Filed: Apr. 29, 2016

(65) Prior Publication Data
US 2016/0320294 A1    Nov. 3, 2016

(30) Foreign Application Priority Data

Apr. 30, 2015 (GB) .................................. 1507440.4

(51) Int. Cl.
| | | |
|---|---|---|
| *G01N 21/35* | (2014.01) | |
| *H01J 49/04* | (2006.01) | |
| *G01N 21/3504* | (2014.01) | |
| *G01J 3/02* | (2006.01) | |
| *G01F 1/00* | (2006.01) | |

(Continued)

(52) U.S. Cl.
CPC ........... *G01N 21/3504* (2013.01); *G01F 1/00* (2013.01); *G01J 3/02* (2013.01); *G01N 21/11* (2013.01); *G01N 21/35* (2013.01); *G01N 21/85* (2013.01); *G01N 33/0009* (2013.01); *H01J 49/0422* (2013.01); *G01N 30/74* (2013.01); *G01N 2030/8868* (2013.01); *H01J 49/24* (2013.01)

(58) Field of Classification Search
CPC .... G01N 21/3504; G01N 21/11; G01N 21/35; G01N 21/85; G01N 30/74; G01N 33/0009; G01F 1/00; G01J 3/02; H01J 49/0422; H01J 49/24
See application file for complete search history.

(56) References Cited

U.S. PATENT DOCUMENTS

| | | | |
|---|---|---|---|
| 9,709,537 B2 * | 7/2017 | Krummen | ............ G01N 30/72 |
| 2011/0201126 A1 * | 8/2011 | Hughes | ............ H01J 49/0422 |
| | | | 436/175 |
| 2013/0116933 A1 | 5/2013 | Geromanos et al. | |

FOREIGN PATENT DOCUMENTS

| | | |
|---|---|---|
| CN | 102928554 A | 2/2013 |
| EP | 1717586 A1 | 11/2006 |

(Continued)

OTHER PUBLICATIONS

Prosser et al, "Rapid Automated Analysis of 13C and 18O of CO2 in Gas Samples by Continuous-flow Isotope Ratio Mass Spectroscopy", Biological Mass Spectrometry, vol. 20, 724-730 (1991).*

*Primary Examiner* — David E Smith
(74) *Attorney, Agent, or Firm* — David A. Schell

(57) ABSTRACT

A system for controlling flow of gas in a continuous flow isotope ratio analyser is provided. The system comprises gas inlet and gas outlet lines for providing gas into and from a measuring cell, and at least one switchable flow restriction on the gas inlet line, for selectively controlling gas flow into the isotope ratio analyser. Also provided is a method for determining an isotope ratio using the system according to the invention.

27 Claims, 2 Drawing Sheets

(51) Int. Cl.
*G01N 21/11* (2006.01)
*G01N 21/85* (2006.01)
*G01N 33/00* (2006.01)
H01J 49/24 (2006.01)
G01N 30/74 (2006.01)
G01N 30/88 (2006.01)

(56) References Cited

FOREIGN PATENT DOCUMENTS

| | | |
|---|---|---|
| EP | 1884761 A1 | 2/2008 |
| JP | 6073336 A | 4/1985 |
| WO | 2005/113830 A2 | 12/2005 |
| WO | 2009/146345 A1 | 12/2009 |
| WO | 2014/096914 A1 | 6/2014 |
| WO | 2014/170179 A1 | 10/2014 |

\* cited by examiner

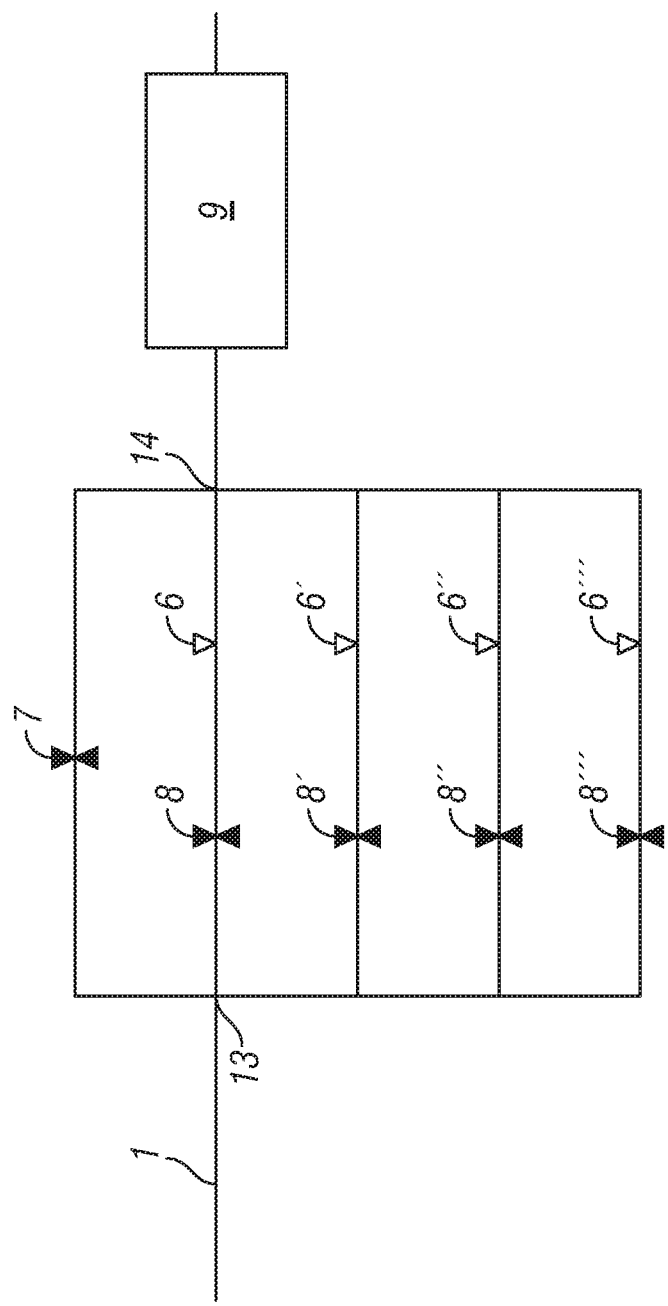

FLOW REDUCTION SYSTEM FOR ISOTOPE RATIO MEASUREMENTS

FIELD

The invention relates to a gas inlet system for isotope ratio analyzers, such as isotope ratio optical spectrometers and isotope ratio mass spectrometers. The invention furthermore relates to a method for delivering a stream of gas to isotope ratio analyzers.

BACKGROUND

The relative abundance of stable isotopes of elements such as carbon, hydrogen, oxygen and nitrogen varies slightly but significantly in various environments. Determination of isotope ratios is a frequently used research tool, for example in forensic, anthropological, biochemical and environmental research, as well as in drug and food industries and for the determination of doping amongst athletes.

Isotope ratio analysis is a methodology for determining the relative abundance of isotopes, for example in gaseous samples containing $CO_2$. For example, isotope ratio analysis can be used to determine the isotope ratios of carbon and oxygen, e.g. $^{13}C/^{12}C$ and/or $^{18}O/^{16}O$. Isotope ratio analysis is most commonly performed by optical spectrometry and mass spectrometry.

Gas inlet systems for isotope ratio analysis are known in the art, especially for mass spectrometers. A general review of isotope ratio mass spectrometry and gas inlet systems is provided by Brenna et al., Mass Spectrometry Reviews, 1997, 16:227-258.

Determination of the isotope ratio of samples usually requires a comparative measurement of the isotope ratio of a sample gas and one or more reference gases with a known isotope ratio. Gas inlet systems for isotope ratio analysis therefore usually comprise an analyte gas inlet, for providing sample and/or reference gas into the analyzer, and a carrier gas inlet, for providing a carrier gas for facilitating transfer of analyte, and that usually does not contain the gas to be determined by the analyzer.

In isotope ratio optical (usually infrared) spectrometry (IROS), photo absorption by $CO_2$ or $H_2O$ is measured and isotope composition determined from the resulting spectra. This methodology has advantages over mass spectrometry, for example due to ease of use, cost and portability. Further, IROS allows direct analysis of $H_2O$, whereas isotope ratio mass spectrometry requires conversion of $H_2O$ to e.g. $H_2$ or $CO_2$, or equilibration with $CO_2$, prior to analysis.

For IROS, however, it is especially critical that the pressure remains constant during the measurement. This is because the isotope ratios are determined by a fit of the adsorption spectrum; the peak shape and width of the adsorption bands depends on the pressure. This is as more important as the fit parameters are optimized for a defined pressure.

Optical cells usually measure samples in a continuous sample flow, or by stop-flow. In a continuous flow, a sample gas is pumped through the optical cell at a constant flow. Pressure is usually maintained by a regulating pump, or by means of a valve at the outlet from the cell. Input into the cell is typically either uncontrolled, i.e. open to atmosphere, or it is controlled by a flow controller. When samples are measured by stopped-flow, the optical cell is flushed with sample, after which the flow is stopped by use of valves at the inlet and outlet of the cell during the measurement time.

A distinct disadvantage of the continuous flow method is that it consumes a large amount of sample, since there is a constant flow of sample through the optical cell during the measurement time. Reducing the flow into the optical cell can reduce sample consumption, but at the same time the response time of the system, i.e. the filling and flush response time, is increased. Stopped-flow however, while reducing the amount of sample that is required, suffers from several drawbacks, such as leaks in the cell, dead volumes and surface effects, that make this method very unstable. For stopped flow it is especially critical that the pressure during the measurement has to be at a defined value and has to be kept constant. Even the switching of a valve normally results in pressure changes, which cannot be compensated in stopped flow technique.

WO 2014/170179 discloses a gas inlet system for introducing gas into an isotope ratio analyzer. The system includes a reference system that comprises supplies of reference and carrier gas that are connected at a mixing junction where they combine. The gases are mixed within a mixing zone and further transported to the isotope ratio analyzer via an exit line, that also comprises an opening.

Sturm et al. (Atmos Meas Tech, 2010, 3:67-77) describe a water vapor isotope analyzer (WVIA, Los Gatos Research Inc), in which the flow of gas can be changed by changing the speed of the pump.

Johnson et al. (Rapid Commun Mass Spectrom, 2011, 25:608-616) discloses a system for an isotope ratio laser spectrometer, that includes a needle valve in front of the analyzer for regulating flow rate.

U.S. Pat. No. 7,810,376 discloses a system for controlling gas flow such that the partial pressure of an analyte gas is held constant. The system includes a controller that controls gas flow in a sample chamber by mixing an inert gas into the chamber so as to keep the partial pressure of the analyte constant.

It would be desirable to provide a gas inlet system for isotope ratio analyzers that provides for rapid analysis of samples while simultaneously minimizing sample loss.

The present invention has been made against this background, to provide a solution to the aforementioned problems and at the same time provide additional advantages as described in the following.

SUMMARY

In accordance with a first aspect of the invention, there is provided a system for controlling gas flow in a continuous flow isotope ratio analyzer, the system comprising
- a measuring cell having an inlet and an outlet for respectively receiving and releasing a gas flow;
- a gas inlet line, fluidly connected to the inlet;
- a gas outlet line, fluidly connected to the outlet; and
- a switchable flow restriction on the gas inlet line, for selectively controlling gas flow into the isotope ratio analyzer.

The invention can also be extended to provide such a gas flow control system in, or in combination with, an isotope ratio analyzer, such as an isotope ratio optical spectrometer, or an isotope ratio mass spectrometer.

According to a further aspect of the invention, there is provided an isotope ratio optical spectrometer having a system for controlling gas flow as described herein.

A further aspect of the invention provides a method of determining an isotope ratio of an analyte gas in a continuous flow isotope ratio spectrometer, wherein the method comprises steps of (i) providing a gas flow comprising an analyte gas into a measuring cell for isotope ratio determination at a first flow rate; (ii) reducing the gas flow into the measuring cell so as to achieve a second flow rate; and (iii) determining the isotope ratio in the analyte. The first and second flow rates are each non-zero flow rates. The second flow rate is preferably lower than the first flow rate, more preferably such that the ratio of the first flow rate to the second flow rate is in the range of 2:1 to 20:1. Preferably, the isotope ratio is determined by measuring the analyte gas when the gas flow into the measuring cell is at the second flow rate, rather than at the first flow rate. In this way, an amount of analyte gas may last longer because it is used at a lower flow rate for the analytical measurement. This enables longer measurement times and thus higher sensitivity for a given amount of analyte gas, while still facilitating to maintain a defined and constant pressure. Preferably, the gas flow into the measuring cell at the first flow rate occurs for a first period, wherein during at least a part of the first period the cell is flushed and/or filled with analyte gas. Further preferably, the gas flow into the measuring cell at the second flow rate occurs for a second period, wherein during at least a part of the second period the gas in the cell is measured to determine the isotope ratio. The continuous flow isotope ratio spectrometer may be an optical or a mass spectrometer, preferably a continuous flow optical spectrometer.

A gas line, in the present context, refers to any channel, tube, conduit, capillary or the like for transporting gas. It will be apparent to the skilled person that additional components can be arranged on the gas line, such as junctions, valves, flow restrictions, flow controllers, gauges and the like. These components can sometimes also be in fluid connection with the gas line.

The switchable flow restriction can be provided by a flow restriction that is arranged on the gas inlet line. A switch of flow can be provided by arranging a gas line that bypasses the gas inlet line along a portion thereof that includes the flow restriction, and is connected to the gas inlet line at a first bypass junction and a second bypass junction, that are upstream and downstream from the flow restriction, respectively. Accordingly, in some embodiments, the switchable flow restriction is provided by a bypass gas line that is connected to the gas inlet line at a first bypass junction and a second bypass junction, and a flow restriction that is arranged on the gas inlet line, between the first and second bypass junction. In this manner, flow can be regulated by selectively directing gas flow into the bypass line and/or the gas inlet line.

In some embodiments, there is a plurality of restrictions arranged on or parallel to the gas inlet line, between the first and second bypass junction. The plurality of restrictions preferably are different restrictions. In this way, the degree of restriction can be selected as required. The restrictions are preferably arranged in parallel arrangement, such that gas flow can be selectively directed into any one restriction. Such arrangement can be suitably accommodated by plurality of gas restriction lines, that meet at a first restriction line junction on the gas inlet line, that is downstream from the first bypass junction, or that meet at the first bypass junction, and that also meet at a second restriction line junction on the gas inlet line, upstream from the second bypass junction, or that meet at the second bypass junction. A restriction, such as a fixed flow restriction can be arranged on each of the gas restriction lines. Thereby, gas flow can be suitably directed into any one, or a plurality of, restrictions that are arranged on the gas restriction lines. Gas flow into the restrictions can be controlled by a suitable arrangement of one or more valves. In one embodiment, there is a switch valve arranged at, or in fluid communication with, the first restriction line junction on the gas inlet, and wherein the position of the switch valve selectively directs gas flow into the restrictions. In another embodiment, there is a valve arranged on each of the restriction gas lines, for selectively regulating flow in each restriction gas line. Alternatively, the plurality of restrictions may be arranged in series arrangement along the gas inlet line, e.g. between the first bypass junction and second bypass junction, preferably configured such that each restriction independently can be bypassed by the bypass line.

Flow control means can in general be provided by any flow controller or regulated valve. Flow control means can for example be a mass flow controller or proportional valve, a volume flow controller, or a switchable combination of fixed flow restrictions that allow flow to be adjusted in discrete steps. Such flow control means are described in e.g. U.S. Pat. No. 7,928,369 and WO 2007/112876. Flow control means can be manually or automatically operated. They can also comprise one or more automatic or manual pressure regulator that is combined with at least one flow restriction downstream of the pressure regulator. Flow control means can be an automatic, electronic or digital flow controller, for example as disclosed in WO 2007/112876. An example of flow control means is the ConFloIV™ from Thermo Scientific.

The flow restriction can thus in general be selected from any convenient means for restricting gas flow, such as mass flow controllers, proportional valves, or fixed flow restrictions. In some preferred embodiments, the flow restriction is a fixed flow restriction. One advantage of providing fixed flow restrictions over flow controllers is the reduced risk of isotope fractionation in the restriction. A further advantage of fixed flow restrictions is shorter response time, compared with flow controllers.

Gas flow into the bypass line can be regulated by one or more valves on the bypass gas line, the gas inlet line, or both. For example, a valve can be arranged between the first and the second bypass junction on the gas inlet line, the valve having a first position in which gas is able to flow between the first and second bypass junction along the gas inlet line, and a second position in which gas is prevented from flowing between the first and second bypass junction along the gas inlet line. Alternatively, or additionally, there can be a valve arranged between the first and the second bypass junction along the bypass gas line, the valve having a first position in which gas is able to flow between the first and second bypass junction along the bypass gas line, and a second position in which gas is prevented from flowing between the first and second bypass junction along the bypass gas line.

In another configuration, flow of gas into the bypass line is regulated by a switching valve that is located at, or in fluid communication with, the first bypass junction. The switching valve can have a first position in which gas is able to flow between the first and second bypass junction along the bypass gas line and in which gas is prevented from flowing between the first and second bypass junction along the gas inlet line, and a second position in which gas is able to flow between the first and second bypass junction along the gas inlet line and in which gas is prevented from flowing between the first and second bypass junction along the bypass gas line. Thereby, using a single valve, unrestricted gas flow can be directed into the bypass line, while a flow restriction on the gas inlet line will restrict the gas flow through the gas inlet line when gas flow is directed through the line and not through the bypass line. This way, a high gas flow can be used, for example for filling and/or flushing the measuring cell of the isotope ratio analyzer, while a reduced flow can be used during measurement (e.g. optical measurement or mass spectrometric measurement), which reduces the amount of gas that is needed for the isotope ratio determination. Alternatively, the measurement may be made for a longer period of time with the given amount of gas thereby enhancing measurement sensitivity.

It will be appreciated that the gas inlet system is compatible for use with other gas inlet systems for delivering analyte (sample and/or reference) and/or carrier gas into isotope ratio analyzers. For example, the gas inlet system can be used in conjunction with the gas inlet systems described in WO 2014/170179 and the co-pending application PCT/EP2014/074205, the entire contents of which are incorporated by reference. Thus, the gas inlet systems for providing analyte gas (sample gas and/or reference gas) and carrier gas as described in these documents, or other suitable gas inlet systems that are known in the art, can be used in conjunction with the flow reduction system described herein.

In some embodiments, gas into the gas inlet system can be provided by an analyte gas inlet line and a carrier gas inlet line that merge at a mixing junction wherein the analyte gas and the carrier gas are combined. The mixing junction can then be fluidly connected to the gas inlet line, so that either analyte gas, carrier gas, or a mixture thereof be provided in the gas inlet system.

There can for example be a variable flow device that provides a supply of analyte flow. Thus, an analyte gas inlet supply can be provided through an intermediate reservoir of variable volume, that can be located downstream from the analyte gas supply and the mixing junction. Through constant decrease of reservoir volume in the intermediate reservoir, a constant flow of analyte gas can be provided. This can be useful when gas from a wide variety of sources is to be analyzed, such as gas from vials, bags, syringes, sampling tubes, gas chromatographs, TOC analyzers, laser desorption instruments, combustion or ablation cells, and so on. Gas from one, or any combination of, such sources can be provided into the variable volume reservoir, and from there it can be delivered to the isotope ratio analyzer.

Valves for controlling flow of gas can further be arranged on the analyte gas inlet line, the carrier gas inlet line or both. Thus a valve for controlling flow of analyte gas towards the mixing junction can be provided. The valve can have a first position in which analyte gas is able to flow along the analyte gas line towards the mixing junction, and a second position in which analyte gas is prevented from flowing along the analyte gas line towards the mixing junction. Similarly, a valve for controlling flow of carrier gas towards the mixing junction can be provided. This valve can also have a first position in which carrier gas is able to flow along the analyte gas line towards the mixing junction, and a second position in which carrier gas is prevented from flowing along the analyte gas line towards the mixing junction.

It may also be suitable to arrange a suitable means for controlling gas flow on the carrier gas line, the analyte gas line, or both. Suitable means for controlling gas flow include mass flow controllers and proportional valves.

In some embodiments, there can be an opening present on the carrier gas inlet line, upstream from the mixing junction. It can be suitable to provide the opening between the valve for controlling flow of carrier gas and the mixing junction. The opening can be open to atmosphere, and thus maintain the system at or near atmospheric pressure. Excess gas that flow through the carrier gas inlet line can exit through the opening.

The flow rate of analyte gas in the analyte gas line can be arranged to be lower than the flow of gas into the isotope ratio analyzer. The mixing junction and the opening can be arranged such that in this configuration, there is a flow of carrier gas along the carrier gas line towards the mixing junction, with excess carrier gas being vented through the opening on the carrier gas inlet line. Thereby, there is always a flow of gas towards the isotope ratio analyzer, and no loss of analyte sample occurs. Back-diffusion of analyte gas towards the opening is prevented by magnitude of gas flow rates in the system and the distance between the mixing junction and the opening.

The opening on the carrier gas inlet line can be open to atmosphere. This ensures that flow in the carrier gas inlet line and the transfer gas line does not exceed that which can be handled by the isotope ratio analyzer. The opening can be in the form of an open capillary. The opening is in some embodiments arranged on a junction, such as a T-junction, upstream of the mixing junction, on the carrier gas inlet line. The opening is structured such that there is little pressure drop across the opening and the pressure at the junction is therefore close to atmospheric pressure. The pressure drop across the opening can be 250 mbar or less, but can also be 100 mbar or less, or 50 mbar or less. In some embodiments, the opening is in the form of an open capillary that is at least 0.5 mm in diameter. The opening can for example be between 0.5 and 2.0 mm in diameter. The opening can further be at least 5 mm, or at least 10 mm, in length. The opening can be in the range of 5-20 mm in length, or about 5-10 mm in length. Although some of the transported gas will be lost through the opening, a suitable amount will be transferred down the carrier gas line and into the transport gas line. It can be preferable that the opening be designed such that negligible pressure drop occurs across it, so that little or no gas is lost through diffusion through the opening. Details of suitable openings are disclosed in WO 2014/170179.

The system can further comprise a supply of analyte gas to supply the analyte gas to the analyte gas inlet line. The analyte gas can be a sample gas, such as a sample gas of unknown isotope composition and/or unknown concentration. The analyte gas can also be a reference gas, i.e. a gas of known isotope ratio, that is for calibration of the isotope ratio analyzer. In some embodiments, the analyte gas is a sample gas. The system can also comprise a supply of carrier gas, for supplying carrier gas to the carrier gas inlet line of the system. The carrier gas can be substantially free of sample gas. In some embodiments, the carrier gas is free of sample gas. In some embodiments, the sample gas is $CO_2$ and the carrier gas is a gas that is free of $CO_2$, such as $CO_2$-free $N_2$, $CO_2$-free He, $CO_2$-free air or $CO_2$-free Ar.

In some embodiments, a water drier is provided on the analyte gas inlet line, for removing traces of water from the analyte gas.

The system can also comprise more than one analyte supply and/or more than one analyte gas inlet line. The system can also comprise more than one carrier gas supply and/or more than one carrier gas inlet line. Thus, modifications and alterations of the system as described herein are possible, while maintaining the particular advantages of the invention as set forth herein, and such modifications will be apparent to the skilled person.

The carrier gas can in general be selected from nitrogen, helium, argon, and air, or it can be a mixture of any two or more of these gases. It can be preferable that the carrier gas be free of sample, i.e. the carrier gas should not contain the sample gas that is to be measured in the isotope ratio analyzer. Common sample gases that are measured by the isotope ratio analyzer include CO, $CO_2$, alkanes, such as $CH_4$, $N_xO_y$, and $NO_2$. It can therefore be preferable that the sample gas be free of one or more of CO, $CO_2$, $CH_4$, $N_xO_y$, and $NO_2$.

Common isotopes that are determined by the isotope ratio analyzer are $^{13}C/^{12}C$ and $^{18}O/^{16}O$, $^{17}O/^{16}O$, $^{15}N/^{14}N$, and $^2H/^1H$. The reference gas can include sample gas that is to be measured for one or more of isotope ratios. For example, the reference gas, with a known isotope ratio, can be dynamically diluted with carrier gas in the system, to provide a plurality of concentrations that are used for measuring the isotope ratio and determine concentration dependence of the isotope ratio.

It can be desirable to selectively control the flow of analyte gas from the analyte gas supply that is delivered through the mixing junction into the gas inlet line. Therefore, in some embodiments, the system can further contain means for controlling flow of analyte gas to the mixing junction, that can for example be a mass flow controller, proportional valve, a volume flow controller, or the like.

The gas inlet system can preferably operate at, or close to, atmospheric pressure. In one configuration, the carrier inlet line and/or the analyte inlet line comprise at least one split that is open to atmosphere.

The analyte gas can be diluted by a flow of carrier gas prior to measurement in the isotope ratio analyzer. For example, a sample gas can be diluted to a concentration that lies within the concentration range of a reference gas with known isotope ratio. The sample gas can for example be diluted to a concentration that lies within the range of concentrations of a reference gas with a known isotope ratio. The sample gas can be diluted by a flow of carrier gas, wherein the sample gas and the carrier gas are mixed at the mixing junction. In some embodiments, the sample gas is not diluted prior to measurement, i.e. the isotope ratio analyzer receives an undiluted sample gas through the gas inlet line.

The analyte gas can also be replaced by, or mixed with, reference gas. The reference gas can be delivered at varying concentration in the stream, by dynamically diluting it with carrier gas. In some embodiments, the reference gas can be provided as a pulse, or a sequential series of pulses of gas with a known isotope ratio.

In certain embodiments, the mixing junction, the first bypass junction and/or the second bypass junction is a T-junction. In this context, a T-junction means any junction of three flow channels, i.e. a junction that contains three arms. The T-junction can be provided as a T-piece, as a Y-piece, or as a junction of three orthogonal channels. The junction can further be provided as a two-dimensional junction, wherein the three channels lie within the same plane, or the junction can be provided as a three dimensional structure, in which the three channels do not all lie in the same plane (i.e., as a three-dimensional "tripod").

Components of the gas line, such as junctions that are described herein, can be provided in a machined block, i.e. as one mechanical piece. This means that manufacturing of the system can be performed by machining out of a bulk of material, such as a metal block. Further, using T-junctions, with or without manufacturing in a machined block, ensures that flow through the openings in the junction are under full mechanical control. The T-junction design ensures that diffusion paths are well separated, which facilitates setup and calibration of the system, because its flow properties are well determined and predictable.

Analyte gas, such as sample gas or reference gas, can be diluted in carrier gas prior to measuring isotope ratio. This can be achieved by mixing carrier gas that is provided through the carrier gas inlet line with analyte gas that is provided through the analyte gas line, at the mixing junction. There can also be a separate mixing device on the analyte gas line, upstream from the mixing junction, as disclosed for example in WO 2014/170179. Accordingly, the sample gas and the reference gas can have a range of concentrations.

Reference gas can be provided through a single supply of reference gas, which is diluted with carrier gas to provide a plurality of concentrations of the reference gas for measuring isotope ratio and its concentration dependence. In some cases, the reference gas is diluted through two stages of dilution.

The gas inlet system can be configured to include at least one controller for controlling valve position of at least one valve. The controller can preferably be adapted so that it can receive an input about at least one parameter that reflects the concentration, isotope ratio or pressure of gas in the system, and provide a signal to the valve based on the parameter information. In some embodiments, the controller is adapted to receive an input about at least one measuring cell parameter, and wherein the controller is able to adjust the position of at least one of the valves in the system based on the at least one measuring cell parameter. The measuring cell parameter can preferably be selected from gas concentration in the measuring cell, isotope ratio determination of a gas in the measuring cell, and gas pressure in the measuring cell.

The controller can receive an input about one measuring cell parameter, and control gas flow in the bypass gas line and/or the gas inlet line, based on the value of the parameter. It can be useful to direct gas flow into the bypass line for a high gas flow during flushing and/or filling of the measuring cell. After flushing and/or filling the cell, it can be useful to switch to a lower flowrate, for example during measurement of a sample at a constant gas flow. Accordingly, the controller can be configured to control the valve position of at least one of the valves so that in a first position gas is directed to flow through the bypass line and into the isotope ratio analyzer at a first flow rate during flushing and/or filling of the isotope ratio analyzer and so that in a second position gas is directed to flow through the flow restriction and into the isotope ratio analyzer at a second flow rate during a measurement of analyte gas in the isotope ratio analyzer, the second flow rate being lower than the first flow rate.

It can be seen, therefore, that generally the gas inlet system can be configured to include at least one controller that is configured to control the switchable flow restriction such that during a first period the gas flows into the measuring cell at a first non-zero flow rate, and during a second period the gas flows into the measuring cell at a second non-zero flow rate that is lower than the first flow rate. Preferably, during at least a part of the first period the cell is flushed and/or filled with analyte gas, and wherein during at least a part of the second period the analyte gas in the cell is measured to determine an isotope ratio of the analyte gas. The controller preferably comprises a computer.

In certain embodiments, the gas inlet system can be provided with at least one gas supply. The gas supply can for example include an analyte gas supply (a sample gas supply and/or reference gas supply) and/or a carrier gas supply. Moreover, the system can include more than one supply of each gas, for example in a configuration that includes multiple reference gas supplies, multiple sample supplies and/or multiple carrier gas supplies. Such supplies can be conveniently provided in systems that have separate gas inlet lines for each gas supply, and that can merge upstream from, or at, the mixing junction.

The gas inlet system can include a gas vacuum pump that can be connected to the gas outlet line. The vacuum pump provides for the possibility of regulating pressure in the measuring cell. Accordingly, there can be provided a pressure sensor operatively connected to the measuring cell, for determining pressure within the measuring cell. The vacuum pump can further be adapted to be controlled in response to a signal from the pressure sensor. For example, the pressure sensor can send a signal to a controller that regulates the setting of the vacuum pump in response to the signal. This pump controller may be, and preferably is, the same controller described above for control of the switchable flow restriction, control of the valves etc. Alternatively, the pump controller may be a separate controller.

The system can further include a gas ballast that is useful for providing an increased dynamic range of the of the pressure control, and also prevents condensation. The gas ballast can be provided as a capillary that can be preferably open to atmosphere, and can be connected to the gas outlet line, between the measuring cell and the vacuum pump. The gas ballast can also be open to a supply of an inert gas. The capillary can further include an adjustable valve, for controlling flow of gas in the capillary. The valve can be adapted to be controlled by a controller that receives a signal from the pressure sensor, e.g. the same controller that controls the pump speed (or a different controller).

In some embodiments, the gas ballast can be provided as a capillary that is fluidly connected to the gas outlet line and that is open to atmosphere. In such embodiments, gas flow through the capillary is regulated by its length and inner diameter.

The gas ballast can also be provided as an orifice on the gas outlet line. In such embodiments, the dimensions of the orifice can be adjusted so as to achieve the required dynamic gas flow desirable for the gas ballast.

It can be advantageous that the system comprise a plurality of gas ballasts, to achieve necessary pressure control in the measuring cell across a wide pressure range. Accordingly, some embodiments relate to a system that comprises a plurality of gas ballasts that can be preferably arranged in parallel. For example, the plurality of gas ballasts can be arranged as a plurality of capillaries that are connected to the gas outlet line, each capillary having specific dimensions of length and diameter, for achieving desirable ballasting. It can be preferable to further include at least one valve for controlling gas flow in the capillaries. In one such embodiment, there can be a switch valve arranged, for selectively directing gas flow through two or more such capillaries. The switch valve can be arranged on the gas outlet line. The switch valve can also be arranged on a gas ballast capillary or gas ballast line, for selectively controlling gas flow in two or more capillaries that meet at the switch valve.

The gas inlet system described herein can be used for providing gas flow to an isotope ratio analyzer. The analyzer can be of any type of analyzer that is capable of determining isotope ratio, for example an isotope ratio mass spectrometer or an isotope ratio optical spectrometer. In some embodiments, the isotope ratio is an isotope ratio optical spectrometer, for example a laser spectrometer. Such spectrometer typically operate in the mid-infrared region, between 2 and 6 μm. In some embodiments, the isotope ratio spectrometer comprises a measuring cell for performing optical absorption measurements on the gas to be analyzed.

The measuring cell can be a flow cell, for example a flow cell for continuous flow of gases. In some embodiments, the measuring cell is a multipass cell, i.e. multipass optical cell, preferably multipass laser cell. The optical pathlength of the cell is typically provided as the sum of the multiple laser passes in the cell, and can be in the range of 1 to $10^5$ m, 1 to $10^4$ m, 1 to $10^3$ m, 1 to 100 m, or 1 to 10 m. A single measuring cell can be used for measuring both sample and reference gases. In some embodiments, the cell is connected to a pump via an outlet of the cell. The pressure in the measuring cell can be in the range of about 50 to 200 mbar, about 70 to 150 mbar or about 80 to 100 mb. In some embodiments, the pressure in the measuring cell is about 100 mb.

In some embodiments, a filter can be provided on the gas inlet line, upstream from the measuring cell, for preventing particles from entering the cell. The filter can be arranged on the gas inlet line between the second bypass junction and the measuring cell.

Isotope ratio in an optical (typically infra red) spectrometer is generally determined by measuring two or more spectral absorption lines, at least one line for each different isotope species to be determined, e.g. one line for $^{13}C^{16}O_2$ and one line for $^{12}C^{16}O_2$. In one example, the preferred spectral line for $CO_2$ is the line at or about 4.329 μm. The ratio of intensities of the spectral absorption lines is a measure of the ratio of the abundance of each isotope species present in the sample, and thus a measure of the isotope ratio (in this case $^{13}C/^{12}C$). Isotope ratio can be expressed by the delta notation (δ), in this case as $δ^{13}C$.

The isotope ratio analyzer used with the gas inlet system described herein can be configured for the determination of isotope ratio $^{13}C/^{12}C$ and/or $^{18}O/^{16}O$ from $CO_2$. In general however, the isotope ratio analyzer can be suitable for determining other isotope ratios, such as $^2H/^1H$ in analysis of e.g. $CH_4$, or for measuring $^{13}C/^{12}C$, $^{18}O/^{16}O$ or $^{15}N/^{14}N$ in other gases, such a for example NO or CO. Other types of gases and the isotope ratios of interest can also be measured, as described further herein, and also as apparent to the skilled person. For measurement of different gases, flow rates and/or gas concentration may need to be adjusted for optimal measurement settings, depending on the nature of the measurement and the sensitivity of the analyzer.

The gas inlet system of the invention provides the opportunity to rapidly change gas flow into an isotope ratio analyzer, that can have distinct advantages. For example, it can be useful and beneficial to be able to rapidly flush the measuring cell prior to, or following, sample analysis, either by carrier gas or by analyte gas prior to analysis. Thus, it can be beneficial to be able to quickly fill the cell with a sample to be analyzed, and then reduce the flow rate during measurement. This minimizes the amount of sample that is required for analysis, and can be particularly useful for samples that are available in minute quantities. Furthermore, the lower flow rate requires less carrier gas during measurement (when sample gas is diluted by carrier gas) or during idle periods of the instrument. Consequently, the reduced, second flow rate may be employed during idle periods of the spectrometer, e.g. when the cell is not being flushed, filled or being used for measurements.

Thus, in the method according to the invention, the measuring cell can be flushed with carrier gas prior to providing flow of sample gas into the measuring cell. The flushing can be performed by allowing gas to flow through the bypass line at a high flowrate, such as about 80 mL/min, and switching to a lower flowrate following the replacement of carrier gas by sample gas. The switching can be performed by means of the valves that regulate flow into the bypass gas line and the gas inlet line.

The above features along with additional details of the invention, are described further in the examples below, which are intended to further illustrate the invention but are not intended to limit its scope in any way.

BRIEF DESCRIPTION OF THE DRAWINGS

The skilled person will understand that the drawings, described below, are for illustration purposes only. The drawings are not intended to limit the scope of the present teachings in any way.

FIG. 3 shows a layout that includes two restriction lines on the gas inlet line of the optical spectrometer.

DESCRIPTION OF VARIOUS EMBODIMENTS

In the following, exemplary embodiments of the invention will be described, referring to the figures. These examples are provided to provide further understanding of the invention, without limiting its scope.

In the following description, a series of steps are described. The skilled person will appreciate that unless required by the context, the order of steps is not critical for the resulting configuration and its effect. Further, it will be apparent to the skilled person that irrespective of the order of steps, the presence or absence of time delay between steps, can be present between some or all of the described steps.

It should be appreciated that the invention is applicable for isotope analysis of gases in general, by optical spectrometry, mass spectrometry or other types of spectrometry techniques. In general, therefore, the gas that is being analyzed in the system will be variable. Further, the system and method according to the invention is illustrated in the embodiments that follow with a preferred embodiment of an optical spectrometer, but it should be appreciated that the invention is also applicable to other spectrometers, including mass spectrometers, for determining isotope ratio.

Figure 1:
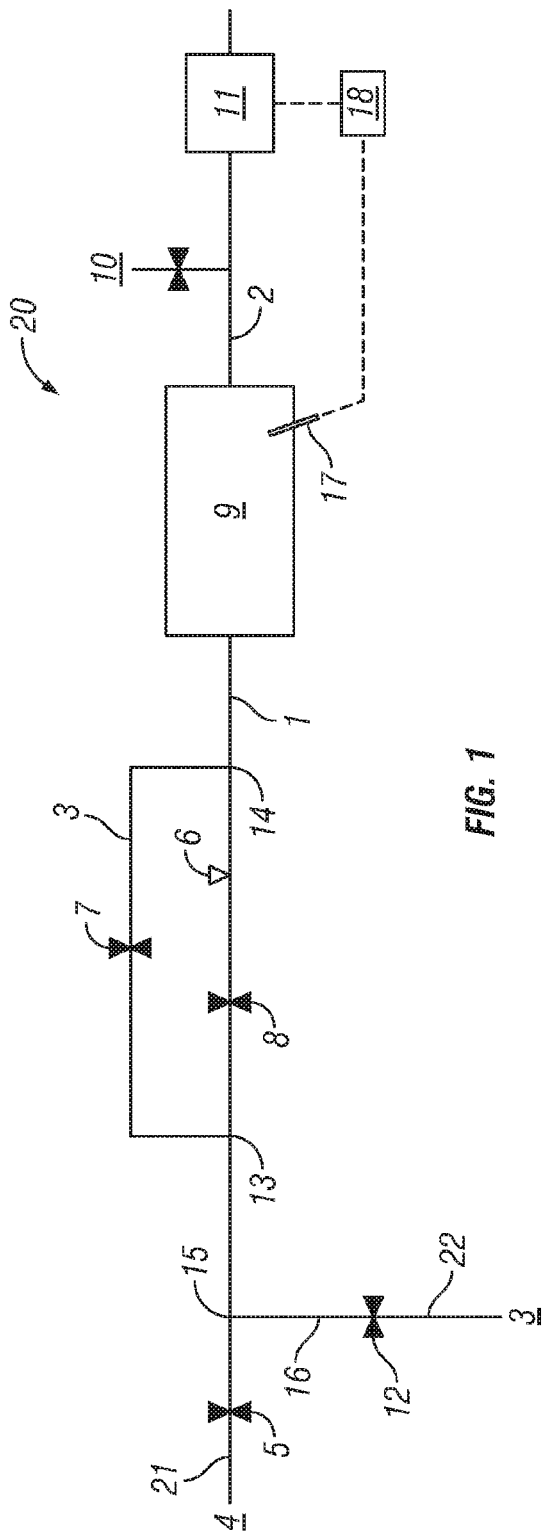
FIG. 1 shows a schematic layout of an isotope ratio optical spectrometer that is interfaced with a gas inlet system according to the invention.

Referring to FIG. 1, there is schematically shown an isotope ratio optical spectrometer 20 that is interfaced with a gas inlet according to the invention. The spectrometer has a gas inlet line 1 and a gas outlet line 2, for providing and removing gas from the measuring cell 9, respectively. The measuring cell is a multipass optical cell. It will be apparent to the skilled person that the isotope ratio optical spectrometer could be replaced by an isotope ratio mass spectrometer that is interfaced with the gas inlet system. The isotope ratio optical spectrometer can be a laser spectrometer, i.e. with the measuring cell as a multipass laser cell. Thus, although the system and method of the invention as described in the embodiments below can be configured with an optical spectrometer, but it should be appreciated that the invention is equally applicable for use with a mass spectrometer or other spectrometers.

An analyte gas (sample gas or reference gas) to be measured is transported from a gas supply (not shown), through an analyte gas inlet line 21 towards the mixing junction 15. From there, the analyte gas travels along the gas inlet line 1 into and through a multi-pass measuring cell 9. The gas transport is driven by a vacuum pump 11, that can for example be a membrane pump. Gas in the gas inlet line can alternatively or additionally be provided by the carrier gas inlet line 22, for example when diluting the analyte gas or for flushing the measuring cell.

A bypass gas line 3 is connected to the gas inlet line 1 at a first bypass junction 13 and a second bypass junction 14. Sample gas that arrives at the first bypass junction therefore can travel along the gas inlet line, along the bypass gas line, or both. Valves 7 and 8 control gas flow along the bypass gas line, and the gas inlet line, respectively. When valve 7 is open (and valve 8 is closed), gas flows along the bypass gas line only and into the measuring cell. Closing valve 7 and opening valve 8 changes the flow, such that gas only flows through the gas inlet line and into the measuring cell. A fixed flow restriction 6 on the gas inlet line, between the first and second junction, reduces gas flow in this configuration.

It can be advantageous to only control gas flow into the bypass line. Thus, another configuration of the system includes a valve 7 for controlling gas flow along the bypass line, but does not include a valve on the gas inlet line between the first and second bypass junction. In this configuration, there will always be gas flow through the fixed flow restriction 6, but a high gas flow can be switched on by opening valve 7 to allow gas flow through the bypass in addition to the gas flow restriction. The advantage of this set up is Reduced cost and complexity (only one valve)

The line with the restriction is always flushed. Otherwise this could be an origin for memory effects There is no valve and thus no potentially dead volume in the low flow line, which could increase the memory and the switching time The line where the valve and the potentially dead volume is located is flushed by a high flow, a dead volume is thus less critical The dimensions of the restriction determine gas flow. In some embodiments, the restriction is configured so as to provide gas flow that is $1/10$ of the gas flow through the bypass line. This means that for a gas flow of 80 mL/min through the bypass gas line, a flow of 8 mL/min will be provided through the restriction on the gas inlet line. Other dimensions of the restriction are possible to achieve the desired gas flow. In some embodiments, the relative gas flow through the restriction compared with the bypass line is about $1/2$ to about $1/20$, about $1/5$ to about $1/15$, or about $1/8$ to about $1/12$. In one embodiment, the relative gas flow through the restriction is about $1/10$ of the gas flow through the bypass line. In other embodiments, the flow restriction 6 may be provided by a mass flow controller or a proportional valve.

It is also possible that the bypass line contain a flow controller, such as a fixed flow restriction or a mass flow controller (not shown) for selectively controlling flow in the bypass gas line.

The gas inlet line may further include a filter (not shown), e.g. a water trap or chemical trap, that is arranged upstream of the measuring cell, and downstream from the second bypass junction 14.

When gas flow into the bypass gas line is prevented by the closed valve 7, gas flows through the gas inlet line towards the measuring cell. In this configuration, gas flow into the measuring cell is limited by the restriction 6 on the gas inlet line.

In a typical setting, a gas flow into the measuring cell is set at 80 mL/min, for pressure at the analyte and/or carrier gas inlet lines that is close to atmospheric pressure. More generally, gas flow in the measuring cell will vary depending on the pressure of the delivered gas. Gas flow into the measuring cell can be achieved through the bypass gas line, by keeping valve 8 closed and valve 7 open (or just valve 7 open in those embodiments where valve 8 is not present). A high flow rate can be desirable for flushing and/or filling the measuring cell. After the measuring cell has been flushed and/or filled at an initial high flow rate, valve 7 is closed, and at the same time valve 8 is opened (or just valve 7 closed in those embodiments where valve 8 is not present). The restriction 6 on the transfer gas line reduces the flow rate into the measuring cell. For example, the restriction can be configured such that that the flow through the restriction is ⅒ of the flow through the bypass. As a consequence, following the filling and/or flushing of the measuring cell through the bypass at e.g. 80 mL/min, a switch to gas flow through the restriction will lead to a reduced flow rate of 8 mL/min.

In general, gas flow through the system is continuous. Gas that flows through the system can be analyte gas, carrier gas, or a mixture of analyte gas and carrier gas. In some configurations, analyte gas is supplemented, i.e. diluted, with carrier gas. This means that when supplied with analyte gas, the system will allow flow of analyte gas through open valve 5 that can be diluted by carrier gas that flows through an open valve 12. The analyte and carrier gas streams merge at the mixing junction 15, where the two gases combine and flow into the measuring cell, either via the bypass line at a high flow rate, or via the gas inlet line through the restriction at a decreased flow rate. If valve 12 is closed, only analyte gas will flow into the measuring cell.

The gas inlet line ensures that all of the sample to be measured is transferred from the sample gas supply to the measuring cell. A constant gas flow into the spectrometer can be ensured by augmenting the flow of sample gas with a flow of carrier gas, which is preferably a sample-free gas. In this way, no sample is wasted. Preferably, the sample gas flow through valve 5 is lower than the flow rate into the measuring cell. Carrier gas will in this configuration flow towards the mixing junction, ensuring that the flow of gas is always towards the measuring cell. If there is little or no sample gas flow, i.e. the concentration of sample gas is close to zero, carrier gas will supplement the gas flow to provide the necessary gas flow into the measuring cell. If there is higher gas flow of sample towards the mixing junction than through the measuring cell, then there will be a backflow of excess sample gas into the carrier gas and through the opening on the carrier gas inlet line. A more detailed description of gas inlet systems that can be combined with the gas inlet system of the present invention is provided in WO 2014/170179.

It can be desirable to further control the flow of analyte gas and/or carrier gas. This can be done by for example including a mass flow controller, a proportional valve, a volume flow controller or the like, on the analyte gas inlet line, on the carrier gas inlet line, or both.

Pressure in the measuring cell is kept constant by controlling pump speed. This can be done by providing a signal from a pressure sensor 17 in the measuring cell to a controller 18 that is connected to and is able to regulate the pump 11. The pump speed is subsequently regulated depending on a comparison of the actual pressure in the cell and a reference setting. Alternatively, the pressure in the measuring cell can be adjusted by adjustment of an adjustable valve between the measuring cell and the vacuum pump. In such configuration, the position of the valve is regulated instead of pump speed by a controller in response to receiving the signal from the sensor. By such means, the pressure in the measuring cell is maintained at a fixed value that is typically in the range of 20 to 200 mbar. In some embodiments, the pressure can be maintained at 40 to 200 mbar, 40 to 150 mbar, or 80 to 120 mbar. In some embodiments, the pressure in the measuring cell can be maintained at about 100 mbar. The analyte gas concentration in the carrier gas is preferably kept constant by the mixing ratio of analyte gas to carrier gas that is set upstream of the switchable flow restriction.

The same controller 18 may also control the valves 7 and 8, and/or valves 5 and 12, or they may be operated by a separate controller (not shown).

For optimizing the flushing of the measuring cell, the cell can be flushed prior to filling. For example, the cell can be flushed using the carrier gas. In some embodiments, the cell can be flushed using zero air, that can be air that is free of sample (such as $CO_2$-free air), or a carrier gas that is free of sample. It can be convenient to use the high-flow bypass gas line for flushing of the cell. After flushing the cell with the carrier gas, the cell can be filled with the sample and/or reference gas. For this purpose, valves 5, 12 regulating gas flow through the carrier gas inlet line and the analyte gas inlet lines can be adjusted to allow the appropriate gas flow. Sample-free carrier gas can therefore be provided by providing carrier gas through the carrier gas inlet line, during which time gas flow through the analyte gas line is prevented by the closed valve 5. In this configuration, carrier gas will flow through the open valve 12, into the gas inlet line and through the bypass line 3, by keeping valve 7 open, for high flow through the bypass gas line. During the flushing procedure, valve 8, if present, should also be opened in order also to flush the gas line of valve 8. Naturally, the flushing of this line can also be performed before or after flushing the cell. After flushing the cell, valve 5 can be opened to allow analyte gas to flow into the measuring cell. Subsequently (e.g. after filling the cell to the desired pressure and concentration with analyte gas), or simultaneously, valve 8 can be opened and valve 7 can be closed, to deliver analyte gas at the reduced flowrate through the restriction 6. The analyte gas can also be mixed with carrier gas if needed, through an open valve 12.

Pressure cycles can be performed to reduce or eliminate effects of dead volumes. This can be achieved by filling the measuring cell with carrier gas or analyte gas, followed by evacuating the cell using the vacuum pump. In this configuration, the bypass gas line is preferably used for filling the cell, by keeping valve 8 closed and valve 7 open. Input from the pressure sensor 17 in the measuring cell can be used to regulate the opening and closing of valves 5 and/or 12. Thus, when the measuring cell is evacuated, both valves are closed, while one or both of the valves can be opened for filling the cell with carrier or analyte gas. The process of filling and evacuating the measuring cell can be repeated one or more times, to effectively remove or minimize dead volumes.

In another configuration, the measuring cell can be evacuated before filling with sample through the high flow bypass. Once the measuring cell has been filled and the base pressure is reached (e.g., a pressure of 100 mbar), the bypass line can be closed and flow through the restriction opened to maintain a slower flow through the measuring cell. The base pressure of the cell is typically reached in about 10 to 300 seconds, but can, depending on flow rate and pressure settings in general be reached in about 5 to 600 seconds.

The switching of flowrates into the measuring cell can also be made dependent on gas concentration, or on a combination of pressure and concentration. For example, the measuring cell can be filled with sample and/or reference gas through the open bypass gas line. Determination of gas concentration in the measuring cell is used to send a signal to a controller for regulating the position of valves 7 and 8. Thus, the measuring cell can be filled with the gas through the open bypass gas line. Once the concentration of a gas to be measured, such as $CO_2$, has reached a predefined threshold, the controller will send a signal so as to close the bypass gas line through valve 7, and direct flow through the fixed flow restriction by opening valve 8 on the gas inlet line.

A similar regulation of gas flow can be done based on determination of isotope ratio in the measuring cell. Thus, based on the determination of isotope ratio, valves 7 and 8 can be adjusted to switch flow from the bypass line and through the restriction, or vice versa, the adjustment being provided by a signal from a gas flow controller.

In another configuration, the measuring cell is evacuated prior to filling with gas for analysis. In such a configuration, the measuring cell is evacuated by the vacuum pump, during which time the valves 7 and 8 are kept closed, to allow for evacuation of the measuring cell. The pressure in the measuring cell is monitored by the pressure sensor, which sends a signal to the controller 18 for adjusting pump speed. After the cell has been evacuated, it can be filled with analyte gas by directing gas flow through the bypass line, by opening valve 7, or alternatively, by directing gas flow through the restriction by opening valve 8.

In some embodiments, in place of valves 7 and 8 the gas inlet could have a single, three-way valve positioned at the first bypass junction 13 to direct gas flow either between the first and the second bypass junction along the gas inlet line (but not along the bypass line), or between the first and second bypass junction along the bypass line (but not along the gas inlet line).

Figure 2:
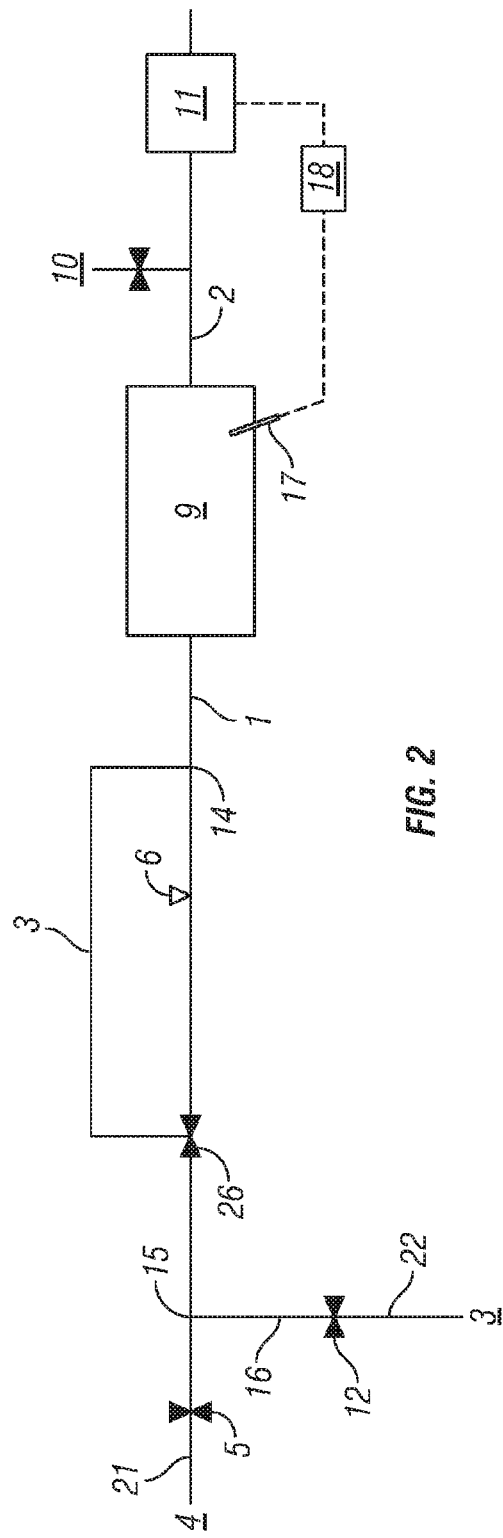
FIG. 2 shows an alternative layout of an isotope ratio optical spectrometer.

In FIG. 2, an alternative arrangement is shown, in which instead of the two valves 7 and 8, a single switch valve 26 is arranged at the first bypass junction 13. The position of the switch valve controls gas flow in the bypass gas line and the inlet gas line, respectively. Thus, in a first position, the switch valve prevents gas flow through the gas inlet line, but allows gas flow through the bypass line. This configuration is useful e.g. during filling and/or flushing of the measuring cell. In a second position, the switch valve prevents gas flow through the bypass gas line, but allows gas flow through the gas inlet line. In this position, gas flow into the measuring cell is regulated by the flow restriction 6. The switch valve can also be provided as a three-way valve that in one position can simultaneously allow gas flow into the bypass gas line and the inlet gas line. In alternate positions, the valve can either allow gas flow into the bypass line, preventing flow through the inlet gas line, or allowing gas flow through the inlet gas line, and preventing flow through the bypass line.

The system can be arranged so as to include a plurality of alternative flow restrictions, that can be arranged in parallel. An illustration of this shown in the embodiment of FIG. 3, in which there are shown four parallel restriction lines on the gas inlet line 1. The four restriction lines meet at the first bypass junction 13, and at the second bypass junction 14. On each restriction line, there is provided a restriction 6, 6', 6", 6'''. Gas flow through each line is controlled by valve 8, 8', 8", 8'''. By means of these valves, a switch between the restrictions can be made, allowing for selective control of gas flow into the measuring cell. For example, in one position, there is a flow of gas through restriction 6, through the open valve 8. Gas flow through the other restrictions 6', 6", 6''' is prevented by the closed valves 8', 8", 8'''. By closing valve 8 and simultaneously opening valve 8', a switch from flow through restriction 6 to restriction 6' can be made. In a similar fashion, by selectively opening and/or closing valves 8, 8', 8", 8''' on the restriction lines, gas flow through one or more of the restrictions can be selectively controlled. The four restrictions are preferably different, so that switch between restrictions results in a change in flow rate into the measuring cell 9. Any number of restriction lines can be arranged in a similar fashion, and additional valves as needed to selectively control gas flow through the restrictions. Furthermore, instead of having separate valves on each restriction line, there can be switch valves arranged at junctions, for example the first bypass junction, for controlling flow into the restriction lines selectively. During gas flow through the restrictions, the bypass line can be closed by means of valve 7 on the bypass line or through a switch valve at the first bypass junction.

As used herein, including in the claims, singular forms of terms are to be construed as also including the plural form and vice versa, unless the context indicates otherwise. Thus, it should be noted that as used herein, the singular forms "a," "an," and "the" include plural references unless the context clearly dictates otherwise.

Throughout the description and claims, the terms "comprise", "including", "having", and "contain" and their variations should be understood as meaning "including but not limited to", and are not intended to exclude other components.

It will be appreciated that variations to the foregoing embodiments of the invention can be made while still falling with the scope of the invention can be made while still falling within scope of the invention. Features disclosed in the specification, unless stated otherwise, can be replaced by alternative features serving the same, equivalent or similar purpose. Thus, unless stated otherwise, each feature disclosed represents one example of a generic series of equivalent or similar features.

Use of exemplary language, such as "for instance", "such as", "for example" and the like, is merely intended to better illustrate the invention and does not indicate a limitation on the scope of the invention unless so claimed. Any steps described in the specification may be performed in any order or simultaneously, unless the context clearly indicates otherwise.

All of the features and/or steps disclosed in the specification can be combined in any combination, except for combinations where at least some of the features and/or steps are mutually exclusive. In particular, preferred features of the invention are applicable to all aspects of the invention and may be used in any combination.

The invention claimed is:

1. A system for controlling gas flow in a continuous flow isotope ratio analyzer, comprising a measuring cell having an inlet and an outlet for respectively receiving and releasing a gas flow;
   a gas inlet line, fluidly connected to the inlet;
   a gas outlet line, fluidly connected to the outlet; and
   at least one switchable flow restriction on the gas inlet line, for selectively controlling gas flow into the isotope ratio analyzer;
   wherein the switchable flow restriction is provided by a bypass gas line that is connected to the gas inlet line at a first bypass junction and a second bypass junction, and a flow restriction that is arranged on the gas inlet line, between the first and second bypass junction; and
   wherein the system further comprises at least one valve for controlling gas flow in the bypass gas line and/or the gas inlet line having at least first and second valve positions wherein in a first position, gas is directed to flow through the bypass line and the isotope ratio analyser at a first non-zero flow rate and wherein in a second position, gas is directed to flow through the flow restriction on the gas inlet line and into the isotope ratio analyser at a second non-zero flow rate different to the first non-zero flow rate.

2. The system of claim 1, wherein the second non-zero flow rate is lower than the first non-zero flow rate.

3. The system of claim 2, wherein the flow restriction is provided by a fixed flow restriction, a mass flow controller or a proportional valve.

4. The system of claim 1, further comprising at least one valve for controlling gas flow in the bypass gas line and/or the gas inlet line.

5. The system of claim 4, wherein the at least one valve comprises a valve arranged between the first and the second bypass junction along the bypass gas line, the valve having a first position in which gas is able to flow between the first and second bypass junction along the bypass gas line, and a second position in which gas is prevented from flowing between the first and second bypass junction along the bypass gas line.

6. The system of claim 4, wherein the at least one valve comprises a switching valve located at, or in fluid communication with, the first bypass junction, the switching valve having a first position in which gas is able to flow between the first and second bypass junction along the bypass gas line and in which gas is prevented from flowing between the first and second bypass junction along the gas inlet line, and a second position in which gas is able to flow between the first and second bypass junction along the gas inlet line and in which gas is prevented from flowing between the first and second bypass junction along the bypass gas line.

7. The system of claim 1, wherein the at least one switchable flow restriction is provided as a plurality of flow restrictions on the gas inlet line that are provided in a parallel arrangement.

8. The system of claim 7, wherein the plurality of restrictions is provided as a plurality of restriction lines, wherein each of the restriction lines comprises at least one flow restriction, wherein the plurality of restriction lines merge at a first restriction line junction, downstream from the first bypass junction, and wherein the plurality of restriction lines merge at a second restriction line junction, upstream from the second bypass junction.

9. The system of claim 1, further comprising an analyte gas inlet line and a carrier gas inlet line that merge at a mixing junction wherein the analyte gas and the carrier gas are combined, and wherein the mixing junction is fluidly connected to the gas inlet line.

10. The system of claim 4, further comprising a controller for controlling valve position of at least one of the valves.

11. The system of claim 10, wherein the controller is adapted to receive an input about at least one measuring cell parameter, and wherein the controller is able to adjust the position of at least one of the valves based on the at least one measuring cell parameter, wherein the at least one measuring cell parameter is selected from gas concentration in the measuring cell, isotope ratio determination of a gas in the measuring cell, and gas pressure in the measuring cell.

12. The system of claim 10, wherein the controller is configured to control the valve position of at least one of the valves so that in a first position gas is directed to flow through the bypass line and into the isotope ratio analyzer at a first flow rate during flushing and/or filling of the isotope ratio analyzer and so that in a second position gas is directed to flow through the flow restriction and into the isotope ratio analyzer at a second flow rate during a measurement of analyte gas in the isotope ratio analyzer, the second flow rate being lower than the first flow rate.

13. The system of claim 1, wherein the measuring cell is a laser cell of an isotope ratio optical spectrometer.

14. The system of claim 1, wherein a vacuum pump is fluidly connected to the gas outlet line.

15. The system of claim 1, further comprising a pressure sensor operatively connected to the measuring cell, for determining pressure within the measuring cell.

16. The system of claim 14, wherein the vacuum pump and/or the adjustable valve is adapted to be controlled in response to a signal from the pressure sensor, optionally to maintain a constant pressure in the measuring cell.

17. The system of claim 14, further comprising at least one gas ballast arranged on the gas outlet line, between the measuring cell and the vacuum pump.

18. The system of claim 17, wherein the gas ballast is provided as (i) a capillary that is fluidly connected to the gas outlet line and that is open to atmosphere, and wherein gas flow through the capillary is regulated by its length and inner diameter, (ii) an orifice on the gas outlet line, or (iii) a capillary that is fluidly connected to the gas outlet line, and an adjustable valve arranged on, or in fluid communication with, the capillary, for regulating gas flow in the capillary.

19. The system of claim 1, further comprising a controller configured to control the switchable flow restriction such that during a first period the gas flows into the measuring cell at a first non-zero flow rate, and during a second period the gas flows into the measuring cell at a second non-zero flow rate that is lower than the first flow rate, wherein during at least a part of the first period the cell is flushed and/or filled with analyte gas, and wherein during at least a part of the second period the analyte gas in the cell is measured to determine an isotope ratio of the analyte gas.

20. A method of determining an isotope ratio of an analyte gas in a continuous flow isotope ratio spectrometer, comprising:
providing a gas flow comprising an analyte gas into a measuring cell for isotope ratio determination at a first flow rate;
reducing the gas flow into the measuring cell so as to achieve a second flow rate; and
determining the isotope ratio in the analyte;
wherein the ratio of the first to the second flow rate is in the range of 2:1 to 20:1.

21. The method of claim 20, wherein the gas flow into the measuring cell at the first flow rate occurs for a first period, wherein during at least a part of the first period the cell is flushed and/or filled with the analyte gas, and wherein the gas flow into the measuring cell at the second flow rate occurs for a second period, wherein during at least a part of the second period the gas in the cell is measured to determine the isotope ratio.

22. The method of claim 20, wherein gas flow is first directed through a first gas line at the first flow rate, and subsequently directed through a second gas line that comprises a flow control means for restricting gas flow, such that gas flows through the second gas line at the second flow rate.

23. The method of claim 22, wherein the flow control means is a fixed flow restriction.

24. The method of claim 22, further comprising flushing the measuring cell with carrier gas prior to the providing a flow of analyte gas.

25. The method of claim 20, wherein the continuous flow isotope ratio spectrometer is an optical spectrometer or a mass spectrometer.

26. A method of determining an isotope ratio of an analyte gas in a continuous flow isotope ratio spectrometer, comprising:
provalyte a gas flow comprising an analyte gas into a measuring cell for isotope ratio determination at a first non-zero flow rate;
reducing the gas flow into the measuring cell so as to achieve a second non-zero flow rate that is lower than the first flow rate; and
determining the isotope ratio in the analyte by measuring the analyte gas when the gas flow into the measuring cell is at the second flow rate.

27. The method of claim 26, wherein the ratio of the first to the second flow rate is in the range of 2:1 to 20:1.

* * * * *